(12) United States Patent
Smith et al.

(10) Patent No.: US 9,347,898 B1
(45) Date of Patent: May 24, 2016

(54) MEASURING THERMAL PROPERTIES OF LAYERED STRUCTURE IN SITU

(71) Applicants: Robert E. Smith, Clarkston, MI (US); Mark A. Hepokoski, Hancock, MI (US)

(72) Inventors: Robert E. Smith, Clarkston, MI (US); Mark A. Hepokoski, Hancock, MI (US)

(73) Assignee: THE UNITED STATES OF AMERICA AS REPRESENTED BY THE SECRETARY OF THE ARMY, Washington, DC (US)

( * ) Notice: Subject to any disclaimer, the term of this patent is extended or adjusted under 35 U.S.C. 154(b) by 477 days.

(21) Appl. No.: 13/962,314

(22) Filed: Aug. 8, 2013

(51) Int. Cl.
  *G01N 25/18* (2006.01)
  *G01K 17/00* (2006.01)

(52) U.S. Cl.
  CPC ...................................... *G01N 25/18* (2013.01)

(58) Field of Classification Search
  CPC ........ G01N 25/18; G01N 25/20; G01K 17/00
  USPC .......... 374/102, 29, 44, 4, 5, 1, 10–12, 30–39
  See application file for complete search history.

(56) References Cited

U.S. PATENT DOCUMENTS

| | | | |
|---|---|---|---|
| 6,054,868 A | | 4/2000 | Borden et al. |
| 6,132,082 A | * | 10/2000 | Pause .............................. 374/43 |
| 6,142,662 A | | 11/2000 | Narh et al. |
| 6,408,256 B1 | | 6/2002 | Hittle et al. |
| 6,676,287 B1 | | 1/2004 | Mathis et al. |
| 6,679,626 B2 | | 1/2004 | Gramckow et al. |
| 7,877,217 B2 | * | 1/2011 | Dankner ......................... 702/35 |
| 7,909,505 B2 | * | 3/2011 | Alexandrov et al. ........... 374/10 |
| 2002/0041619 A1 | * | 4/2002 | Merzliakov et al. ............ 374/44 |
| 2007/0047614 A1 | * | 3/2007 | Lee et al. ......................... 374/44 |
| 2015/0219674 A1 | * | 8/2015 | Hornig et al. ................... 374/44 |

OTHER PUBLICATIONS

Jaarinen and Luukkala, Numerical Analysis of Thermal Waves in Stratified Media for Non-Distructive Testing Purposes, Journal, Oct. 1983, 6 Pages, Department of Physics, University of Helsinki, Finland.

Belattar, Thermal Non-Destructive Characterization by the Thermal Transfer Function and the Numerical Method of Control Volumes, Internet NDT.net, Aug. 2003, 7 Pages, vol. 8 No. 08, Morocco.

Model, Thermal Transport Properties of Layered Materials: Identification by a New Numerical Algorithm for Transient Measurements, International Journal of Thermophysics, Jan. 2005, pp. 165-178, vol. 26, No. 1.

Ramu and Bowers, Analysis of the "3-Omega" Method for Substrates and Thick Films of Anisotropic Thermal Conductivity, Journal of Applied Physics 112, 043516 (2012) Published: Aug. 30, 2012, pp. 043516-1-043516-8, University of California, California.

* cited by examiner

*Primary Examiner* — Gail Kaplan Verbitsky (57) ABSTRACT

An in situ method for deriving the thermal properties of a layered structure represents physical layers by effective thermal layers. The method requires access to only one side of a structure and performs a series of tests wherein a periodic heat flux is applied to the surface of the structure. Each test employs a unique frequency, which is associated with an effective thermal layer of the structure. During the tests the temperature of the surface is monitored and a record of transient temperature is kept. A thermal model of effective layers is created based on the number of tests/frequencies available. The values of the applied heat fluxes are incorporated into this thermal model of effective layers. An optimization technique is used to find the thermal capacity and thermal resistance of the effective layers by best matching the predicted response to that of the measured transient temperature response.

20 Claims, 4 Drawing Sheets

REAL

| TIME | TEMP (°C) | q |
|---|---|---|
| 0 | 30 | 3000 |
| 1 | 34 | 3200 |
| 2 | 32 | 3300 |
| 3 | 34 | 3400 |
| 4 | 38 | 3600 |
| 5 | 36 | 3800 |
| 6 | 39 | 4000 |
| . | . | . |
| . | . | . |
| . | . | . |

FIG. 5

VIRTUAL

| TIME | TEMP (°C) | q |
|---|---|---|
| 0 | $T_1$ | 3000 |
| 1 | $T_2$ | 3200 |
| 2 | $T_3$ | 3300 |
| 3 | $T_4$ | 3400 |
| 4 | $T_5$ | 3600 |
| 5 | $T_6$ | 3800 |
| 6 | $T_7$ | 4000 |
| . | . | . |
| . | . | . |
| . | . | . |

… 
MEASURING THERMAL PROPERTIES OF LAYERED STRUCTURE IN SITU

GOVERNMENT INTEREST

The invention described here may be made, used and licensed by and for the U.S. Government for governmental purposes without paying royalty to us.

BACKGROUND OF THE INVENTION

1. Field of the Invention

Our invention falls within the field of non-destructive testing and more particularly falls within the area of non-destructive testing to ascertain thermal qualities of structures or materials. Our method is applicable to testing anisotropic layered structures by observing surface temperature changes during the course of a controlled heating of the surface.

2. Background Art

Various techniques are known and used to ascertain thermal properties of layered structures wherein heat is applied to the structure and temperature changes at the surface or an interface are observed. In these techniques experimental data is used, via modeling and optimization or error minimization processes to derive thermal properties such as thermal conductivity or thermal diffusivity. See, for example, a paper by Model in *International Journal of Thermophysics*, Vol. 26, No. 1, January 2003 titled "Thermal Transport Properties of Layered Materials: Identification by a New Numerical Algorithm for Transient Measurements." That paper contemplates a mathematical model wherein a flat, planar heat source is sandwiched at the interface between two identical layered structures. The use of lowered surface heat excitation frequencies to elicit thermal responses of deeper zones within a structure was discussed in "Thermal Non-Destructive Characterization by the Thermal Transfer Function and the Numerical Method of Control Volumes" by Bellatar et al., at NDT.net August 2003, Vol. 8 No. 8.

SUMMARY OF THE INVENTION

Generally, the present invention provides an improved in situ method for deriving the thermal properties of a layered structure wherein the material properties of the layers vary and the thickness of the layers also vary. The physical layers of the structure are treated as being regrouped into thermally effective layers. We regard a thermally effective layer as consisting of a generally layer-shaped planar zone of the structure which behaves thermally as a unit since the zone has a single, characteristic heat capacity value and a single, characteristic heat conductivity value. The improved method requires access to only one side of a layered structure so that, for example, only the exterior surface of a military vehicle's layered hull minor needs to be accessed to determine thermal qualities of the armor. The improved method further includes performing a series of tests wherein a sinusoidal heat flux is applied to the surface of the structure. A single frequency of heat flux input is found and used for each test in the series and a given test in the series uses a different frequency than other tests. Each frequency is associated with a thermally effective layer of the structure. During the tests the temperature of the surface is monitored such that a graph of temperature change over time, or transient temperature, can be plotted. By various optimization techniques, the transient temperature data can be used to derive the thermal capacity and thermal conductivity of the effective thermal layers. Our method can be applied to homogeneous, one-layer structures as well as to anisotropic layered structures.

DETAILED DESCRIPTION OF THE PREFERRED EMBODIMENT(S)

Definitions and Terminology

The following definitions and terminology are applied as understood by one skilled in the appropriate art.

The singular forms such as "a," "an," and "the" include plural references unless the context clearly indicates otherwise. For example, reference to "a material" includes reference to one or more of such materials, and "an element" includes reference to one or more of such elements.

As used herein, "substantial" and "about", when used in reference to a quantity or amount of a material, dimension, characteristic, parameter, and the like, refer to an amount that is sufficient to provide an effect that the material or characteristic was intended to provide as understood by one skilled in the art. The amount of variation generally depends on the specific implementation. Similarly, "substantially free of" or the like refers to the lack of an identified composition, characteristic, or property. Particularly, assemblies that are identified as being "substantially free of" are either completely absent of the characteristic, or the characteristic is present only in values which are small enough that no meaningful effect on the desired results is generated.

Concentrations, values, dimensions, amounts, and other quantitative data may be presented herein in a range format. One skilled in the art will understand that such range format is used for convenience and brevity and should be interpreted flexibly to include not only the numerical values explicitly recited as the limits of the range, but also to include all the individual numerical values or sub-ranges encompassed within that range as if each numerical value and sub-range is explicitly recited. For example, a size range of about 1 dimensional unit to about 100 dimensional units should be interpreted to include not only the explicitly recited limits, but also to include individual sizes such as 2 dimensional units, 3 dimensional units, 10 dimensional units, and the like; and sub-ranges such as 10 dimensional units to 50 dimensional units, 20 dimensional units to 100 dimensional units, and the like.

Figure 1:
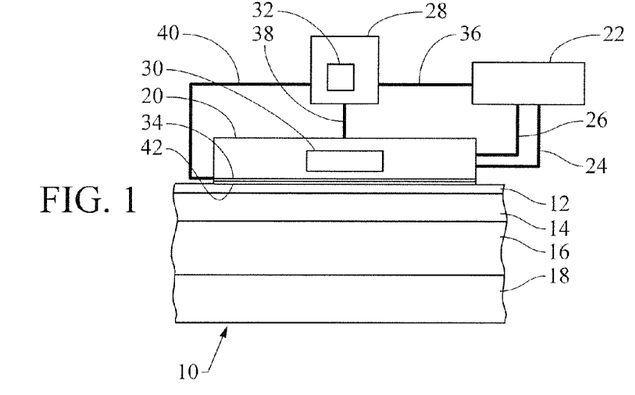
FIG. 1 is a diagram of the portion of a test apparatus used to generate heat waves in the structure to be tested.

FIG. 1 shows diagrammatically the portion of the test apparatus used in our method to generate the sinusoidal heat waves in the structure to be tested. The layered structure 10 is typically a multi-layered armor structure such as one might find on an armored military vehicle. Structure 10 as shown has individual layers 12, 14, 16 and 18 but structure 10 can have any number of layers. The thickness and material composition of the layers can vary. By way of example only, for layered armor, the material composition of individual layers can be any metal, such as steel, aluminum or other metal or a metallic alloy; a layer may be comprised of a ceramic material such as alumina or can be comprised of a glass material; a layer may be comprised of a rubber or plastic material; or a layer may be comprised of a structural composite of two or more material elements. Depending on the application, layer thickness can be quite thin and film-like as would be the case with protective coatings or coverings; alternately, the layers can be several feet or more thick as would be the case with road and road bed structures. The materials of layers can include those used on any item having a layered structural element.

A modified thermoelectric heating device 20 is placed atop layered structure 10. Device 20 alternately heats and cools structure 10, and the heating element of device 20 can be any heating element found in commercially available thermoelectric devices. Cooling is done by active refrigeration as opposed to merely allowing heat previously imparted to structure 10 to escape to the surrounding environment. Accordingly, a refrigeration unit 22 provides chilled coolant to device 20 via coolant line 24 and receives used coolant from device 20 via return line 26. Device 20 alternately heats and cools structure 10, and measures the temperature of structure 10 at the interface between device 20 and structure 10. Heating and cooling occurs in a continuous cycle so that the thermal flux at the interface between device 20 and structure 10 is, preferably, a sinusoidal function of time with a characteristic frequency. Although the aforementioned function is preferred to be sinusoidal, the function merely needs to exhibit a periodic, cyclic ebb and flow of heat flux at the interface between device 20 and structure 10. Thus, for example, the function can be a quasi-sinusoidal function such as a saw tooth function or a function where the curvature is not precisely sinusoidal.

The heat flux between device 20 and structure 10 is measured by a thin film heat flux sensor 34 closely adhered to and congruent with the bottom of device 20. The value for heat flux can be calculated based on the electrical inputs to refrigeration unit 22 and device 20, but it is preferred to measure heat flux directly with sensor 34. The heating and cooling of device 20 is governed by a control unit 28, by logic circuitry 30, or by a combination of unit 28 and circuitry 30. Circuitry 30 is typically a circuit board built into device 20 and control unit 28 is typically a personal computer or a laptop computer having a monitor screen 32. Heat flux sensor 34 includes at its center a temperature sensor, designated as reference numeral 51 in FIG. 4, which typically is a thermocouple type of sensor. Control unit 28 communicates with refrigeration unit 22, thermoelectric device 10, flux sensor 34 and temperature sensor 51 by respective lines or channels 36, 38 and 40.

Thermal interface material in the form of a thin thermal gap pad 42 is disposed between sensor 34 and structure 10, the pad minimizing the thermal interface resistance due to irregularities or roughness of the surface of structure 10 where device 20 is positioned. The thickness and thermal qualities of such pads from any supplier are quite uniform and controlled by suppliers of such pads. The pad's thermal qualities can be easily be treated in any calculations by which thermal qualities of structure 10 are derived from heat flux and temperature readings at the interface between thermoelectric device 20 and structure 10. Other thermal interface materials in the form of grease, paste or tape can be used and in some cases it may be unnecessary or not preferred to use a thermal interface material.

Figure 2:
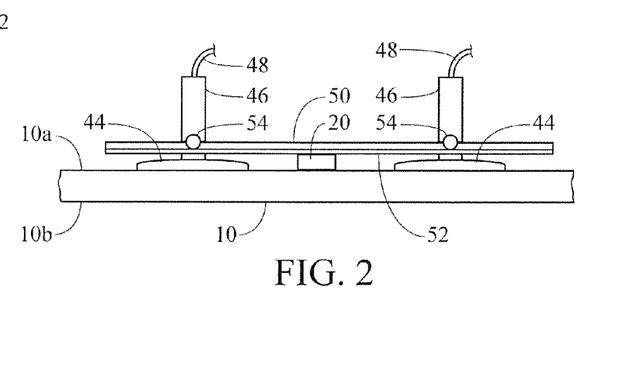
FIG. 2 shows the portion of the test apparatus by which a thermoelectric device is held on the structure to be tested.

FIG. 2 diagrammatically shows the portion of the test apparatus by which thermoelectric device 20 is held on structure 20 during testing of structure 10, many of the details in FIG. 1 being omitted for convenience. The apparatus includes suction cups 44 that adhere to the surface of structure 10 and post-like cylinders 46 that are attached to the suction cups. The cylinders communicate with both vacuum lines 48 and suction cups 44 so that air or other fluid can be evacuated from the cups. Affixed to cylinders 46 are a pair of parallel beams or rails 50, which preferably have flanges 52 bearing upon device 20 to hold device 20 in place upon structure 10. The position of rails 50 can be adjusted by turning knobs 54 to loosen the rails' connection with cylinders 46, repositioning the rails and then turning the knobs to lock the rails in their new positions.

The apparatus of FIG. 2 is advantageous in that the surface upon which device 20 bears can be tilted at any angle and can even be facing downward. Consequently layered armor structures on vehicles can be tested using this apparatus no matter what the angular orientation of the armor structure is, so that testing armored structures under field conditions is feasible. Additionally, the test apparatus shown in FIGS. 1 and 2 is highly portable in that it weighs less than 50 pounds and no component need have a longest dimension greater than about two and one-half feet. In these figures all portions of the test apparatus are disposed upon or are faced by surface 10a of layered structure 10; no sensor or other test equipment is disposed upon of faced by opposed surface 10b of structure 10.

Our method for deriving the thermal properties of a layered structure involves treating the structure as if it were a slab of semi-infinite thickness, a slab bounded by one planar surface but having an infinite thickness. It can be shown from an analytic solution involving a semi-infinitely thick slab exposed to a surface heat flux (i.e. the semi-infinite solid solution) that the following relatively simple closed form equation (Equation 1) can be obtained relating material properties of interest to surface heat flux and temperature:

$$k\rho c_p = \frac{4t}{\pi}\left(\frac{q_{\prime\prime s}}{Ts - Ti}\right)^2 \quad (1)$$

In this equation k is the conductivity of the material, p is the density of the material, $c_p$ is specific heat of the material, t is the elapsed time, $q_s''$ is the heat flux imposed at the surface, $T_i$ is the initial surface temperature and $T_s$ is the surface temperature at elapsed time t. Thus if t, $q_s''$. $T_i$ and $T_s$ are known, it is possible to find the product on the left side of Equation 1, a product whose factors are the conductivity, density, and specific heat of a semi-infinitely thick slab.

When heated continuously on one side, a given specimen of layered structure will for a short time behave thermally as a slab of semi-infinite thickness and its thermal qualities can be derived by Equation 1. The specimen acts in accordance with Equation 1 until the temperature of opposite, unheated side begins to be significantly influenced by the heat source. Thus a layered armor structure heated on the front side will act thermally as a semi-infinitely thick slab until the back face ceases to have an essentially constant temperature and begins to exhibit a steady temperature rise with time. Our experiments show that, depending on the exact composition, thickness and number of layers in an armor recipe, specimens of actual armor will behave thermally as semi-infinitely thick slabs for several minutes or less when continuously heated on one face by a constant two to four Watt source.

To expand the time window during which layered structure 10 armor acts as a slab of semi-infinite thickness, one can vary the heating method by replacing the continuous heating technique with the sinusoidal heating and cooling cycle described above. In the most preferred method the cooling part of the cycle removes an amount of heat from structure 10 equal to the amount of heat imparted to structure 10 during the heating portion of the cycle. By this method the opposed surface or back face 10b remains at a constant temperature indefinitely so that device 20 can be operated continuously, thereby allowing any number of heating-cooling cycle frequencies to be applied and tested efficiently in a single, uninterrupted trial session. Despite the fact that surface or face 10b remains at a constant temperature, the portion of surface or face 10a at the interface of device 20 and structure 10 will vary over time as the structure is subjected to various frequencies of sinusoidal heating-cooling cycles.

Figure 3:
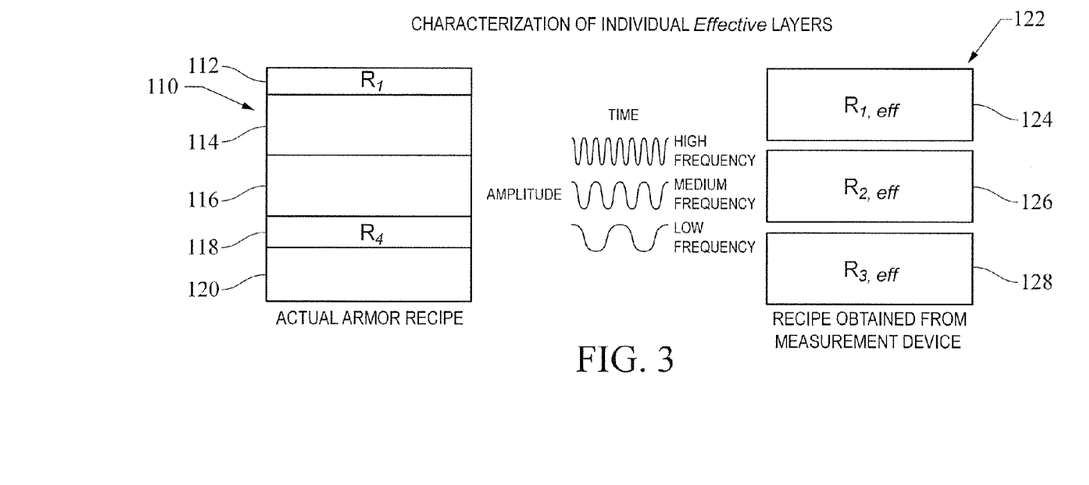
FIG. 3 shows how the physical layers of a structure are converted to thermally effective layers for purposes of modeling and simulation.

Treating layered structures as semi-infinitely thick slabs, as discussed in connection with Equation 1 above, is an important aspect of our method for creating a thermal model of a known layered structure utilizing varied frequencies of heating-cooling cycles. Creation of a thermal model is best explained by example in conjunction with FIG. 3. In that figure a known layered armor structure is designated at 110 having individual layers of armor material 112, 114, 116, 118 and 120. The thickness, area, location within structure 110 and material of each of these layers is known. Also known for each layer are k (the conductivity of the material), p (the density of the material), $c_p$ (the specific heat of the material), and C (the heat capacity of the material). The heat capacity and thermal conductivity for structure 110 as a whole are known as well.

A test apparatus like that shown in FIGS. 1 and 2 is utilized except that structure 110 replaces structure 10 in those figures. Device 20 imparts heating-cooling cycles to one exposed surface of structure 110 at various frequencies. For most layered structures, and for most multi-layered armor structures, testing with two or more frequencies is necessary or at least desired. Typically the selected frequencies include a low frequency, a medium frequency and a high frequency. As a rule of thumb, the low frequency is in the range of approximately $10^{-4}$ Hz to $10^{-3}$ Hz, the medium frequency is in the range of approximately $10^{-3}$ Hz to $10^{-2}$ Hz and the high frequency is in the range of approximately $10^{-2}$ Hz to $10^{-4}$ Hz. Layers at or near the bottom (or the face opposite where device 20 is located) of a layered structure thermally respond well to low frequencies and do not respond as well to medium or high frequencies. Layers in the middle of a structure 10 or 110 tend to best respond thermally to medium frequencies and layers at or near the top (or the face where device 20 is located) respond well thermally to high frequencies.

For each of the chosen heating cooling cycle frequencies there is for thermal modeling purposes an effective thermal layer, which has its own characteristic thermal conductivity (or alternately, thermal resistance, R) and has its own characteristic heat capacity. The effective thermal layers are the components of a thermal model of a layered structure. Accordingly, in FIG. 3 thermal model 122 of structure 110 is comprised of thermal effective layers 124, 126 and 128; in FIG. 3 the thermally effective layers are labeled as having respective characteristic resistances of $R_{1,\mathit{eff}}$ and $R_{2,\mathit{eff}}$ and $R_{3,\mathit{eff}}$.

Figure 4:
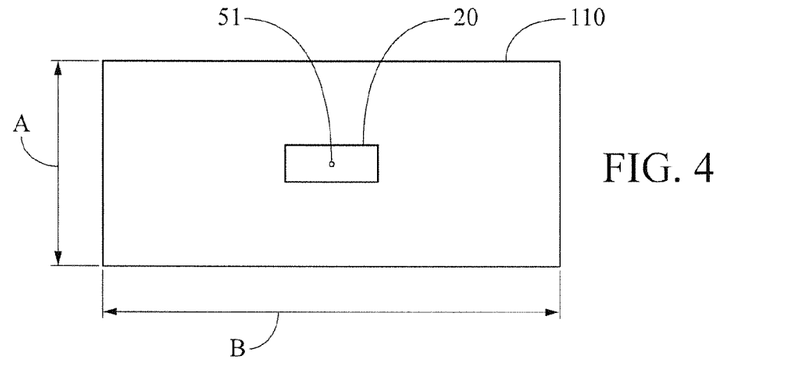
FIG. 4 shows the location of a thermoelectric device and temperature sensor at the exposed face of a layered structure to be tested.

The method of determining the thermally effective layers of a structure involves using a test specimen whose width and length are preferably known so that the heat capacity for the thermally effective layers is more conveniently found. Thus as seen in FIG. 4, the width "A" and the length "B" of layered structure 110 are known and are typically one foot and two feet, respectively. The specimen is typically surrounded by an adiabatic environment in that any exposed face of structure 110 or any exposed edges of the structure's layers contacted by adiabatic materials, such as a body of air or wood or insulating foam, having a higher thermal resistance than any of the physical layers of the structure. Thermoelectric device 20 is typically centered on the exposed face of the layered structure and a temperature sensor, schematically shown at 51 is disposed at the center of the interface between device 20 and the exposed surface of structure 110. To determine the thermal qualities of the first effective layer, the layer contacted by device 20, the first layer is somewhat arbitrarily assumed to have a thickness $t_1$. For example, in a layered structure whose overall thickness is 2.0 inches, $t_1$ can be presumed to be 0.50 inches or 0.75 inches or another selected value. Preferably, if the dimensions A, B and $t_1$ are known or presumed, the volume of the first thermally effective layer can be determined, and the specific heat $c_{p1}$ of the first effective layer is then a direct-proportion function of its heat capacity $C_1$. Hence in our discussions of the qualities of thermally effective layers, we often refer to a layer's specific heat in lieu of its heat capacity since one quality determines the other in our method.

Figure 5:
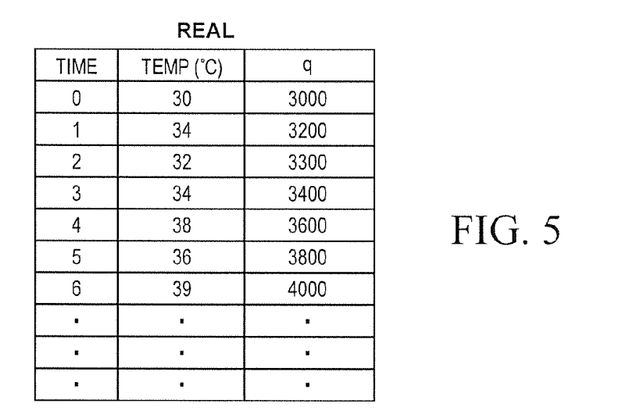
FIG. 5 is a representative data table showing temperatures and heat flux values at chosen time intervals during sinusoidal heating and cooling of the tested layered structure.

As discussed previously, the thermal qualities of the thermally first effective layer of structure 110 are found by applying a set of a high frequency sinusoidal heating-cooling cycles by means of device 20. A table of data such as that in FIG. 5 is kept. In the table, for regular time intervals, the temperature and heat flux (q, or Watts per unit area) are recorded; the time intervals can be, for example, one second long or can be orders of magnitude longer or shorter, depending on the circumstances of the test. Next, a second thermally effective layer is treated by applying a second set of heating-cooling cycles at a lower frequency than was used for the first effective layer; a second data table, again similar to that in FIG. 5, is generated. The process of applying successively lower heating-cooling frequencies for additional thermally effective layers and creating additional associated data tables continues until the desired number of thermally effective layers has been processed. Typically, for a layered armor structure one to two inches thick, three effective thermal layers are determined, although any number of effective layers can be found in a given case, depending mainly on the accuracy of one's instruments and the level of effort one wishes to expend. For some applications it is not necessary to know the overall thickness or depth of the structure, and characterizing a selected number of upper layers will suffice. This would be the case, for example, when characterizing the thermal characteristics of layers of material of, and under, a road or other cases where the structure can be treated as if it were infinitely thick. As another example, this would also be the case where only the outer layer or a set of outer layers are of interest. It is also possible to have a single thermally effective layer for a structure, particularly when the structure is monolithic or has layers of thermally similar material.

The values for the thermal conductivity or the thermal resistance of effective layers as well as the heat capacity values or specific heat values for these layers is are then derived. This is done by a thermal solver program or thermal simulation program in conjunction with an optimization code. Numerous thermal solver tools or thermal simulation computer programs are commercially available and may be used for our method. For the sake of being complete in our disclosure, and not by way of recommendation, we note that we used the thermal solver, MuSES, or Multi-Service Electro-optics Signature code, which inter alia is useful for computer-aided-design modeling as applied to thermal behavior of multi-component structures. There are also numerous methods to achieve optimization, including the Levenberg-Marquardt method, or Nelder-Mead based optimizers. A discussion of optimization techniques used in thermal modeling of layered structures can be found in a paper by Regine Model in *International Journal of Thermophysics*, Vol. 26, No. 1, January 2003 titled "Thermal Transport Properties of Layered Materials: Identification by a New Numerical Algorithm for Transient Measurements." Again, for the sake of being complete in our disclosure, and not by way of recommendation, we note that we used optimization code found in Mode-FRONTIER, a known multi-objective optimization and design environment.

Figure 6:
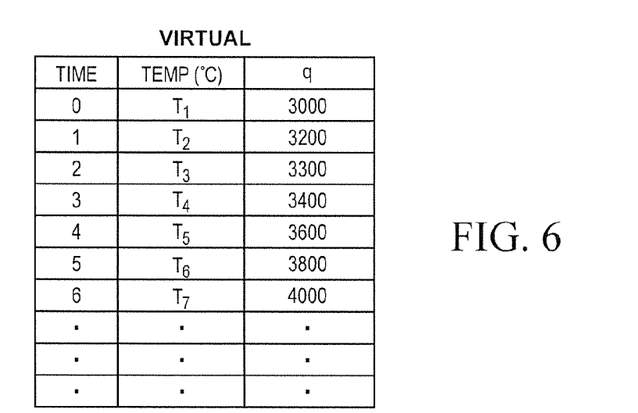
FIG. 6 is a representative data table showing temperatures and heat flux values at chosen time intervals during simulated sinusoidal heating and cooling of the a thermal model of the layered structure.

Using the thermal solver program, a thermal model or virtual representation of structure 110 is created having effective thermal layers corresponding to those of structure 110. The values for conductivity or resistance and for capacity or specific heat for each effective layer are arbitrarily picked. For a given effective layer, if these picked values are incorrect, then the temperature changes as output by the model will not match the temperature changes experienced by structure 110 for the same heat flux inputs. On the other hand, for a given effective layer, if these picked values are accurate, then the temperature changes as output by the model will closely match the temperature changes experienced by structure 110 for the same heat flux inputs 110. In FIG. 6 is shown a typical "virtual" data table associated with a given effective layer of the thermal model or virtual representation of structure 110. The "Time" and "q" columns of the FIG. 6 table have the same entries as the respective "Time" and "q" columns of the FIG. 5 "Real" table. The values $T_1$, $T_2$, $T_3$ ... in FIG. 6 may or may not show temperature changes matching those in FIG. 5, depending on the values for conductivity or resistance and capacity or specific heat which have been chosen. The optimization technique is used to try, for each effective layer, combinations of values for conductivity or resistance and capacity or specific heat for the model until the temperature changes shown by the model emulate temperature changes reflected by the actual testing of structure 110 as represented by the real data table in FIG. 5.

Figure 7:
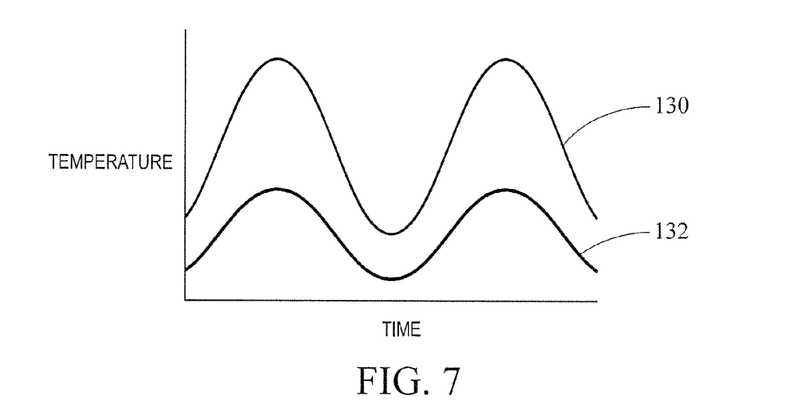
FIG. 7 is a graph of typical transient temperature curves associated with a given thermally effective layer, the curves corresponding to real heating of the tested structure and simulated heating of the modeled structure.

The real changes in temperature over time, or transient temperature, for a thermally effective layer of structure 110 can be depicted graphically, as by curve 130 in FIG. 7. The data points for curve 130 are taken from a real data table such as that shown in FIG. 5. It will be seen that curve 130 has a sinusoidal shape as a consequence of the sinusoidal heating-cooling cycles generated by thermoelectric device 20. Curve 130 is typical but the precise shape of the curve will vary from one effective layer to another. Curve 130 serves as a standard or benchmark for the transient temperature readings produced by the corresponding effective layer in the thermal model of structure 110, whose data points are derived from a virtual data table such as that depicted in FIG. 6. Thus if the picked values for conductivity or resistance and capacity or specific heat for the model are accurate, the curve the representing the temperature changes shown by the model will have the same, or essentially the same, shape as curve 130. But if the picked values for conductivity or resistance and capacity or specific heat for the model are not accurate, the curve the representing the temperature changes produced by the model will not have the same shape as curve 130; in such a case the curve the representing the temperature changes produced by the model can have a shape, for example like curve 132 in FIG. 7.

Figure 8:
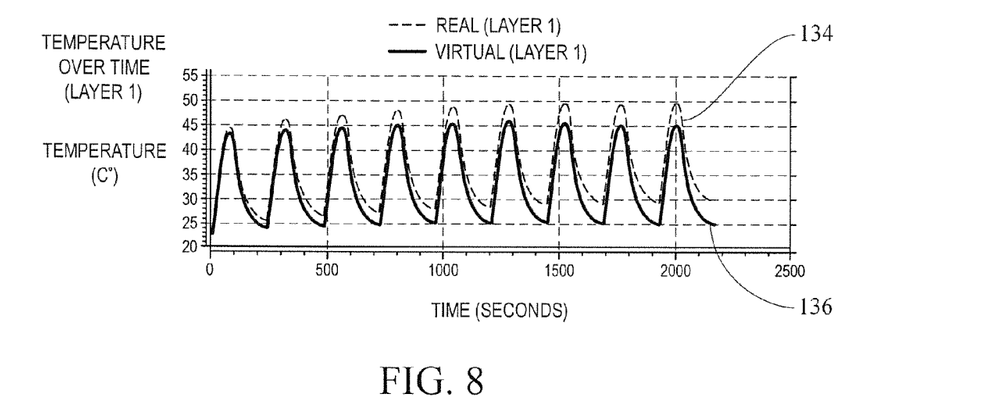
FIG. 8 shows a comparison of derivatives of transient temperature curves for both the real structure tested and the thermal simulation thereof.

In FIG. 8 is shown an analysis graph wherein curve 134 depicts the slopes at a continuum of points along the curve derived from a real data table like the one in FIG. 5. Any conventional method to derive the slope of a function can be used to generate curve 134. As a matter of choice, we used the following fourth order central difference approximation, Equation 2 below, to characterize the slope of the transient temperature response.

$$f'(x_i) = \frac{f(x_{i-2}) - 8f(x_{i-1}) + 8f(x_{i+1}) - f(x_{i+2})}{12h} \qquad (2)$$

Curve 136 depicts the slopes at a continuum of points along the curve derived from a virtual data table like the one in FIG. 6. We have found that the use of an analysis graph such as that shown in FIG. 8 is a useful way to compare the transient temperature curves for real and virtual data for a given thermally effective layer in a layered structure. Various data analysis techniques can be used to determine the closeness of fit between curves 134 and 136. Additionally, if preferred, such techniques can be applied directly to compare real data curves such as curve 132 to their virtual data counterparts.

Figure 9:
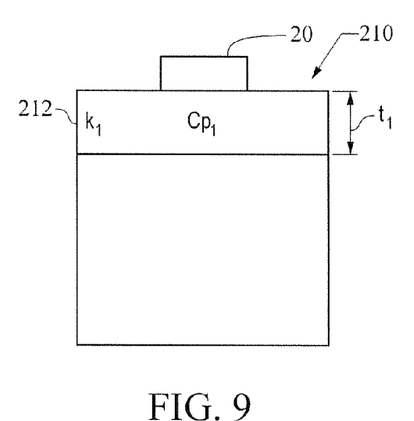
FIG. 9 through 11 are a series of representations of a layered structure illustrating the characterization of a succession of thermally effective layers in the structure.
Figure 10:
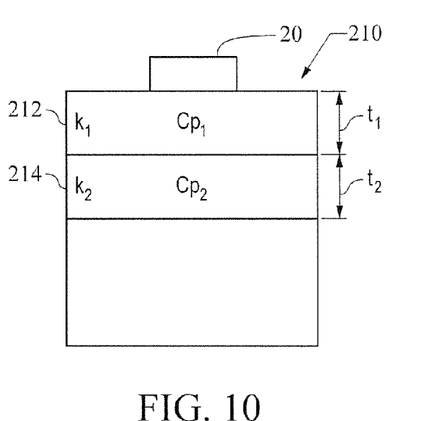
Figure 11:
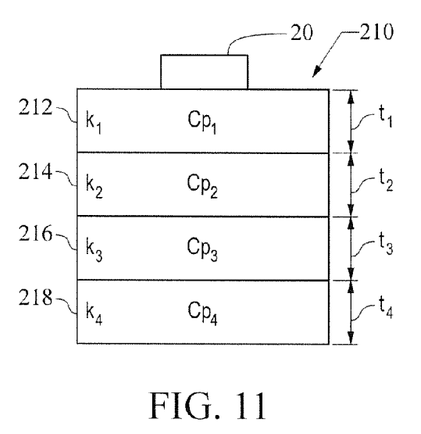

One slight variation of our method is to find the first thermally effective layer of structure 110, then create a virtual representation of that effective layer, and then find optimized values for conductivity or resistance and for heat capacity or specific heat for the virtual representation of the first thermally effective layer; this process is repeated for the second and subsequent effective layers. Otherwise the techniques of our method remain the same. The variation of our method is further explained in conjunction with FIGS. 9 through 11. In FIG. 9 device 20 applies sinusoidal heating-cooling cycles to a layered structure 210 in the same fashion as was done for structure 110. The first thermally effective layer 212 is assumed to have thickness $t_1$ and the appropriate time, temperature and heat flux readings are taken. Optimized values for conductivity and specific heat, $k_1$ and $c_1$ respectively, are derived for layer 212. Then, as seen in FIG. 10, a second thermally effective layer 214, presumed to have a thickness $t_2$ has the appropriate time temperature and heat flux readings recorded. Optimized values for $k_2$ and $c_{p2}$ are derived for layer 214. The foregoing process is repeated for the third and subsequent effective layers. FIG. 10 represents completion of the variation of our method as applied to structure 210 having four thermally effective layers, 212, 214, 216 and 218 having respective presumed thicknesses, $t_1$, $t_2$, $t_3$, and $t_4$.

Figure 12:
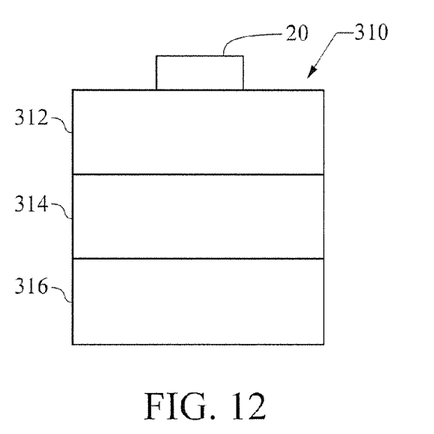
FIG. 12 is a representation of a layered structure illustrating a variation in the method of characterizing thermally effective layers.

A second variation of our method is explained in conjunction with FIG. 12, wherein the second variation of our method is applied to a layered structure 310. The difference between the second variation of our method and what is discussed above is as follows. In the second variation, we find the first thermally effective layer 312 using a high frequency of heating-cooling cycles applied by device 20. Then we find the bottom or third thermally effective layer 316 by using a low frequency of heating cooling cycles applied by device 20. Finally, we find a second or middle thermally effective layer 314 using a medium frequency of heating cooling cycles applied by device 20. Determining the optimized values for each effective layer can occur either just after the transient temperature and heat flux readings are taken for that layer or after the readings for all the layers have been taken.

In one particular application of our method thermally effective layers may represent actual material layers which may be determined if the number of actual layers is known and their thicknesses are known or determined by testing, physical measurement, manufacturer specification sheets, drawings or other means. In a case where even more information is known, as for example when the thermal properties of one actual/thermally effective layer are known, accurate characterization of the remaining layers is facilitated. In another particular application of our method, one can determine thermal characteristics near non-uniformities in the specimen; for example, one can thermally characterize layered structure adjacent a door opening by building a model incorporating the door opening or selected edges thereof and associated measurements.

In some cases the match between the modeled thermal qualities and the previously known, reference thermal qualities of structures 10 or 110 may be less close than desired in view of the purposes for which the model is created. For example if the model is created for quality control purposes or damage inspection purposes, a variance, however statistically or mathematically determined, of greater than 10% may be undesirable. In such a case an additional frequency is found which causes a temperature rise at the interface between device 20 and the exposed surface of structure 10 or 110. Finding this frequency, as well as finding the frequencies initially used, can be done by trial and error over the course of numerous tests; however the applicants herein have found that as experience grows with our method, one is able to choose frequencies with less and less experimentation. The additional frequency leads to an additional thermally effective layer for the thermal model of layered structure 10 or 110, and the model is revised by adding the additional effective layer and adjusting the presumed thickness of the initially found effective layers if necessary. The revised model is then tested in the same fashion as the original model. The foregoing process of revising the thermal model can be repeated until an acceptable accuracy of the model is achieved.

Once the model is complete, it can be used for various purposes. One purpose is quality control in a production setting where layered structures are produced. A thermal model with effective thermal layers is first created using a first sample of the product, a quality-standard sample known to have been manufactured properly and known to be defect free. Then a second sample of the product is subjected to heating-cooling cycles at the same frequencies selected to model the first sample. If the thermal conductivity or thermal resistance or thermal capacity of the second sample does not match that of the first sample, then there is an indication that the second sample was not manufactured properly or else has a defect. In similar fashion, a sample of a layered product that has been used in the field can be compared to a sample known to be free of defects. For example the layered armor on a military vehicle may have been hit by enemy fire, and comparing the conductivity, resistance and capacity of the effective thermal layers of vehicle armor to those of a defect-free sample will help ascertain whether the vehicle armor has been damaged internally.

Various alterations and modifications will become apparent to those skilled in the art without departing from the scope and spirit of this invention and it is understood this invention is limited only by the following claims.

What is claimed is:

1. A method to characterize thermal properties of a structure, comprising:
   using a specimen of the structure;
   subjecting the specimen at an exposed face to one or more sets of periodic heating-cooling cycles;
   taking temperature measurements and obtaining heat flux values only at the exposed face;
   for each set of the cycles, using a cycle frequency unique to the set;
   associating with each set of the cycles a real thermally effective layer of the structure, the real thermally effective layer having a presumed thickness;
   for each unique frequency and its associated real thermally effective layer, recording the times and recording the temperature measurements and heat flux values during an associated set of the cycles to which the specimen is subjected;
   for each real thermally effective layer, creating a representation of real transient temperature data caused by the associated set of cycles;
   creating a thermal simulation of the structure having a virtual thermally effective layer corresponding to each real thermally effective layer of the structure;
   for each virtual thermally effective layer determining either a heat conductivity value or a heat resistance value, and determining either a heat capacity value or a specific heat value, comprising the sub steps of:
      assigning one value for either heat conductivity or heat resistance and assigning another value for either heat capacity or specific heat;
      for the virtual thermally effective layer using the one value and the other value to produce a representation of the virtual transient temperature data resulting from a simulated application of an appropriate set of the heating-cooling cycles from a corresponding real thermally effective layer;
      comparing the representations of the real transient temperature data and the virtual transient temperature data;
      repeating the foregoing sub steps until a satisfactory match between the representations found.

2. The method of claim 1 wherein:
   the sub step of comparing the representations comprises comparing slopes associated with the virtual data to slopes associated with the real data to determine closeness of fit between the virtual data and the real data.

3. The method of claim 1 wherein:
   the representation of the real data can be expressed as one graph;
   the representation of the virtual data can be expressed as another graph;
   the sub step of comparing the representations comprises comparing the one graph to other graph by determining closeness of fit of curves respectively for the one graph and the other graph.

4. The method of claim 1 wherein the specimen is a first specimen of the structure known to meet a selected standard, the method further comprising:
- providing a second specimen of the structure;
- characterizing the thermal qualities of the second specimen in the same fashion as done for the first specimen;
- making a comparison of the heat conductivity value or the heat resistance value derived for the second specimen to the heat conductivity value or the heat resistance value derived for the first specimen;
- making a comparison of the heat capacity value or the specific heat value derived for the second specimen to the heat capacity value or the specific heat value derived for the first specimen;
- based on the comparisons, deciding whether the second specimen meets the selected standard.

5. The method of claim 1 wherein a portable apparatus is used to subject the specimen to the sets of the heating-cooling cycles and to obtain the heat flux values and take temperature measurements.

6. The method of claim 5 wherein the apparatus includes means for holding a thermoelectric device on the exposed face during any angular orientation of the exposed surface.

7. The method of claim 1 wherein the unique frequencies include a high frequency, a mid range frequency and a low frequency.

8. The method of claim 7 wherein the unique frequencies include only one high frequency, only one mid range frequency and only one low frequency.

9. The method of claim 2 wherein the structure is a monolithic structure having a single real thermally effective layer.

10. A method to characterize thermal properties of a structure having one or more layers comprising:
- providing a specimen of the structure;
- at an exposed face of a surface layer of the specimen, subjecting the specimen in situ to sets of periodic heating-cooling cycles wherein heating is done by a thermoelectric device and cooling is done by active refrigeration;
- taking temperature measurements and obtaining heat flux values only at the exposed face;
- for each of the sets of cycles, using a cycle frequency unique to the set;
- associating with each unique frequency a real thermally effective layer of the structure, each of the real thermally effective layers having a presumed thickness;
- for each of the unique frequencies and their associated real thermally effective layers recording the times and recording the temperature measurements and obtaining the heat flux values for the set of the heating-cooling cycles to which the specimen is then subjected;
- for each of the real thermally effective layers creating a real representation of a transient temperature data caused by an appropriate set of the heating-cooling cycles;
- creating a thermal simulation of the layered structure having virtual thermally effective layers corresponding to the real thermally effective layers of the structure;
- for each virtual thermally effective layer determining either a heat conductivity value or a heat resistance value and for each virtual thermally effective layer determining either a heat capacity value or a specific heat value, comprising the sub steps of:
  - assigning one value for either heat conductivity or heat resistance and assigning another value for either heat capacity or specific heat;
  - for each virtual thermally effective layer use the one value and the other value to produce a virtual representation of the transient temperature data resulting from a simulated application of an appropriate set of heating-cooling cycles from a corresponding real thermally effective layer;
  - comparing the virtual representation to the real representation;
  - repeating the foregoing sub steps in an optimization process until a satisfactory match between the virtual representation and the real representation is found.

11. The method of claim 10 wherein the sub step of comparing the virtual representation to the real representation comprises comparing slopes associated with the virtual representation to slopes associate d with the real representation.

12. The method of claim 11 wherein a portable apparatus is used to subject the specimen to the sets of the heating-cooling cycles, obtain the heat flux values and take the temperature measurements.

13. The method of claim 12 wherein the apparatus includes means for holding a thermoelectric device on the exposed face during any angular orientation of the exposed face.

14. The method of claim 10 wherein:
- the real representation can be expressed as one graph;
- the virtual representation can be expressed as another graph;
- the sub step of comparing the virtual representation to the real representation comprises comparing the one graph to other graph by determining closeness of fit of curves respectively for the one graph and the other graph.

15. An in situ method to characterize thermal properties of a structure having one or more layers wherein the layered structure is treated as a semi-infinitely thick slab, the method comprising:
- providing a specimen of the structure wherein the width and length of each layer are known and the thickness of each layer is presumed;
- surrounding the specimen with adiabatic material;
- at an exposed face of a surface layer of the specimen, subjecting the specimen in situ to sets of sinusoidal heating-cooling cycles wherein heating is done by a thermoelectric device and cooling is done by active refrigeration;
- taking temperature and heat flux measurements only at the exposed face;
- for each of the sets of the cycles, using a cycle frequency unique to the set;
- associating with each unique frequency a real thermally effective layer of the structure, each of the real thermally effective layers having a presumed thickness;
- for each of the unique frequencies and their associated real thermally effective layers recording times, temperatures, and heat flux for the set of the heating-cooling cycles to which the specimen is then subjected;
- for each of the real thermally effective layers creating a real representation of a transient temperature function caused by the set of the heating-cooling cycles;
- creating a thermal simulation of the layered structure having virtual thermally effective layers corresponding to the real thermally effective layers of the structure;
- for each virtual thermally effective layer determining either a heat conductivity value or a heat resistance value and for each virtual thermally effective layer determining either a heat capacity value or a specific heat value, comprising the sub steps of:
  - assigning one value for either the heat conductivity value or the heat resistance value and assigning another value for either the heat capacity value or the specific heat value;

for each virtual thermally effective layer use the one value and the other value to produce a virtual representation of the transient temperature function resulting from a simulated application of the appropriate set of the heating-cooling cycles from a corresponding real thermally effective layer;

comparing the virtual representation to the real representation;

repeating the foregoing sub steps in an optimization process until a satisfactory match between the virtual representation and the real representation is found.

16. The method of claim 15 wherein the sub step of comparing the virtual representation to the real representation comprises comparing slopes associated with the virtual representation to slopes associate d with the real representation.

17. The method of claim 16 wherein the unique frequencies include a high frequency, a mid range frequency and a low frequency.

18. The method of claim 16 wherein:

the real representation can be expressed as one graph;

the virtual representation can be expressed as another graph;

the sub step of comparing the virtual representation to the real representation comprises comparing the one graph to other graph by determining closeness of fit of curves respectively for the one graph and the other graph.

19. The method of claim 16 wherein a portable apparatus is used to subject the specimen to the sets of the heating-cooling cycles, take the heat flux measurements and take the temperature measurements.

20. The method of claim 18 wherein the apparatus includes means for holding a thermoelectric device on the exposed face during any angular orientation of the exposed surface.

* * * * *